United States Patent [19]

Hagmann et al.

[11] Patent Number: 5,629,343

[45] Date of Patent: May 13, 1997

[54] N-(MERCAPTOACYL) PEPTIDYL DERIVATIVES AS ANTIDEGENERATIVE AGENTS

[75] Inventors: William Hagmann, Westfield; Ihor Kopka, Millburn, both of N.J.

[73] Assignee: Merck & Co., Inc., Rahway, N.J.

[21] Appl. No.: 392,730

[22] PCT Filed: Sep. 27, 1993

[86] PCT No.: PCT/US93/09137

§ 371 Date: Feb. 23, 1995

§ 102(e) Date: Feb. 23, 1995

[87] PCT Pub. No.: WO94/07481

PCT Pub. Date: Apr. 14, 1994

[51] Int. Cl.$^6$ .................................................. A61K 31/21
[52] U.S. Cl. .................... 514/513; 514/562; 514/616; 564/154; 558/254; 562/426
[58] Field of Search .................... 564/154; 558/254; 562/426; 514/513, 562, 616

[56] References Cited

U.S. PATENT DOCUMENTS 5,061,710  10/1991  Haslanger .............................. 514/266

FOREIGN PATENT DOCUMENTS

| | | |
|---|---|---|
| 0038046A2 | 10/1981 | European Pat. Off. . |
| 0232027A2 | 8/1987 | European Pat. Off. . |
| 0254032A2 | 1/1988 | European Pat. Off. . |
| 0274234A2 | 7/1988 | European Pat. Off. . |
| 0341081A2 | 11/1989 | European Pat. Off. . |
| 0489577A1 | 6/1992 | European Pat. Off. . |
| 0489579A1 | 6/1992 | European Pat. Off. . |

*Primary Examiner*—Samuel Barts
*Attorney, Agent, or Firm*—Curtis C. Panzer; David L. Rose

[57] ABSTRACT

Novel N-(mercaptoacyl)peptidyl compounds are useful as inhibitors of matrix metalloendoproteinases which degrade major components of articular cartilage and basement membranes causing degenerative diseases such as arthritis, periodontal disease, corneal ulceration, are described. For example, N-(2-thiomethyl-4-phenyl-butanoyl)-L-leucinamide was prepared and its inhibitory activity against stromelysin was tested in vitro.

13 Claims, No Drawings

N-(MERCAPTOACYL) PEPTIDYL DERIVATIVES AS ANTIDEGENERATIVE AGENTS

This application is a 371 of PCT/US93/09137 filed Sep. 27, 1993.

BACKGROUND OF THE INVENTION

Novel N-(mercaptoacyl)peptidyl compounds of formula (I) are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophobic epidermolysis bullosa, coronary thrombosis associated with atherosclerotic plaque rupture, and aneurysmal aortic disease. The matrix metalloendoproteinases are a family of zinc-containing proteinases including but not limited to stromelysin, collagenase, and gelatinase, that are capable of degrading the major components of articular cartilage and basement membranes. The inhibitors claimed herein may also be useful in preventing the pathological sequelae following a traumatic injury that could lead to a permanent disability. These compounds may also have utility as a means for birth control by preventing ovulation or implantation.

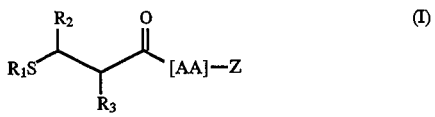

The disability observed in osteoarthritis (OA) and rheumatoid arthritis (RA) is largely due to the loss of articular cartilage. No therapeutic agent in the prior art is known to prevent the attrition of articular cartilage in these diseases.

"Disease modifying antirheumatic drugs" (DMARD), i.e., agents capable of preventing or slowing the ultimate loss of joint function in OA and RA are widely sought. Generic nonsteroidal antiinflammatory drugs (NSAIDs) may be combined with such agents to provide some relief from pain and swelling.

Stromelysin (aka. proteoglycanase, matrix metalloproteinase-3, MMP-3, procollagenase activator, "transin"), collagenase (aka. interstitial collagenase, matrix metalloproteinase-1, MMP-1, Type II collagenase), and gelatinase (aka. type IV collagenase, matrix metalloproteinase-2, MMP-2, 72kDa-gelatinase or type V collagenase, matrix metalloproteinase-9, MMP-9, 95kDa-gelatinase) are metalloendoproteinases secreted by fibroblasts and chondrocytes, and are capable of degrading the major connective tissue components of articular cartilage or basement membranes. Elevated levels of both enzymes have been detected in joints of arthritic humans and animals: K. A. Hasty, R. A. Reife, A. H. Kang, J. M. Stuart, "The role of stromelysin in the cartilage destruction that accompanies inflammatory arthritis", Arthr. Rheum., 33,388–97 (1990); S. M. Krane, E. P. Amento, M. B. Goldring, S. R. Goldring, and M. L. Stephenson, "Modulation of matrix synthesis and degradation in joint inflammation", in The Control of Tissue Damage", A. B. Glauert (ed.), Elsevier Sci. Publ., Amsterdam, 1988, Ch. 14, pp 179–95; A. Blanckaert, B. Mazieres, Y. Eeckhout, G. Vaes, "Direct extraction and assay of collagenase from human osteoarthrtic cartilage", Clin. Chim. Acta, 185 73–80 (1989). Each enzyme is secreted from these cells as an inactive proenzyme which is subsequently activated. There is evidence that stromelysin may be the in vivo activator for collagenase and gelatinase, implying a cascade for degradative enzyme activity: A. Ho, H. Nagase, "Evidence that human rheumatoid synovial matrix metalloproteinase 3 is an endogenous activator of procollagenase", Arch Biochem Biophys., 267,211–16 (1988); G. Murphy, M. I. Crockett, P. E. Stephens, B. J. Smith, A. J. P. Docherty, "Stromelysin is an activator of procollagenase", Biochem. J., 248, 265–8 (1987); Y. Ogata, J. J. Enghild, H. Nagase, "Matrix metalloproteinase 3 (stromelysin) activates the precursor for human matrix metalloproteinase 94, J. Biol. Chem., 267, 3581–3584 (1992). Inhibiting stromelysin could limit the activation of collagenase and gelatinase as well as prevent the degradation proteoglycan.

That stromelysin inhibition may be effective in preventing articular cartilage degradation has been demonstrated in vitro by measuring the effect of matrix metalloendoproteinase inhibitors on proteoglycan release from rabbit cartilage explants: C. B. Caputo, L. A. Sygowski, S. P. Patton, D. J. Wolanin, A. Shaw, R. A. Roberts, G. DiPasquale, J. Orthopaedic Res., 6, 103–8 (1988).

There is an extensive literature on the involvement of these metalloproteinases in arthritis, but there is very little to guide one in developing a specific inhibitor for each enzyme.

In preliminary studies of rabbit proteoglycanase with substrates and inhibitors, little was found to indicate the enzyme's requirements for hydrolysis or inhibition beyond a preference for hydrophobic residues at the $P_1'$ position: A. Shaw, R. A. Roberts, D. J. Wolanin, "Small substrates and inhibitors of the metalloproteoglycanase of rabbit articular chondrocytes", Adv. Inflam. Res., 12, 67–79 (1988). More extensive studies with a series of substrates revealed that stromelysin will tolerate nearly every amino acid residue around the scissile bond: G. B. Fields, H. Brikedal-Hansen, H. E. Van Wart, unpublished results presented at the Matrix Metalloproteinase Conference, Sept. 1989, Sandestin Fla.

Human rheumatoid synovial collagenase has been shown to share ~50% homology with human stromelysin: S. E. Whitham, G. Murphy, P. Angel, H. J. Rahmsdorf, B. J. Smith, A. Lyons, T. J. R. Harris, J. J. Reynolds, P. Herrlich, A .J. P. Docherty, "Comparison of human stromelysin and collagenase by cloning and sequence analysis", Biochem. J., 240,913–6 (1986). Many collagenase inhibitors have been designed around the cleavage site of the α-chain sequence of Type II collagen: W. H. Johnson, N. A. Roberts, N. Brokakoti, "Collagenase inhibitors: their design and potential therapeutic use", J. Enzyme Inhib., 2,1–22 (1987). One such inhibitor, N-[3-(benzyloxycarbonyl) amino-1-carboxy-n-propyl]-L-leucyl-O-methyl-L-tyrosine, N-methylamide, prepared at G. D. Searle, Inc., and shown to be a potent inhibitor of human rheumatoid synovial collagenase ($IC_{50}$= 0.8 μM), was also found to inhibit rabbit bone proteoglycanase ($IC_{50}$=0.5 μM): J. M. Delaisse, Y. Eeckhout, C. Sear, A. Galloway, K. McCullagh, G. Vaes, "A new synthetic inhibitor of mammalian tissue collagenase inhibits bone resorption in culture", Biochem. Biophys. Res. Commun., 133, 483–90 (1985).

Gelatinase (MR ~72,000) has been isolated from rheumatoid fibroblasts: Y. Okada, T. Morodomi, J. J. Enghild, K. Suzuki, A. Yasui, I. Nakanishi, G. Salvesen, H. Nagase, "Matrix metalloproteinase 2 from human rheumatoid synovial fibroblasts", Eur. J., Biochem., 194, 721–30 (1990). The synthesis of the proenzyme is not coordinately regulated with the other two metalloproteinases and its activation may also be different. The role of gelatinase in the tissue destruction of articular cartilage appears different from the other two enzymes and, therefore, its inhibition may provide additional protection from degradation. A higher molecular weight gelatinase (MR ~95,000; aka. type-V collagenase, matrix metallo-proteinase-9, MMP-9) is also secreted by fibroblasts and monocytes and may be involved in cartilage degradation.

From the significant proportion of homology between human fibroblast collagenase, stromelysin, and gelatinase it is expected that a compound that inhibits one enzyme may have a similar effect on all of them.

Compounds that inhibit collagenase, which possess structural portions akin to those of the instant invention include those encompassed by U.S. Pat. No. 5,109,000 issued Apr. 28, 1992; U.S. Pat. No. 4,595,700, issued Jun. 17, 1986; U.S. Pat. No. 4,371,466, issued Feb. 1, 1983. Also included are compounds encompassed by claims in foreign applications EP423,943, EP273,689, EP322184, EP185,380, and WO8806890.

It is believed that stromelysin and collagenase inhibitors have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case, J. Sano, R. Lafyatis, E. F. Remmers, G. K. Kumkumian, R. L. Wilder, "Transin/stromelysin expression in the synovium of rats with experimental erosive arthritis", J. Clin Invest., 84, 1731–40 (1989); R. J. Williams, R. L. Smith, D. J. Schurman, "Septic Arthritis: Staphylococcal induction of chondrocyte proteolytic activity", Arthr. Rheum., 33, 533–41 (1990).

It is also believed that inhibitors of stromelysin, collagenase, and gelatinase will be useful to control tumor metastasis, optionally in combination with current chemotherapy and/or radiation. See L. M. Matrisian, G. T. Bowden, P. Krieg, G. Furstenberger, J. P. Briand, P. Leroy, R. Breathnach, "The mRNA coding for the secreted protease transin is expressed more abundantly in malignant than in benign tumors", Proc. Natl. Acad. Sci., U.S.A, 83, 9413–7 (1986); S. M. Wilhelm, I. E. Collier, A. Kronberger, A. Z. Eisen, B. L. Marmer, G. A. Grant, E. A. Bauer, G. I. Goldberg, "Human skin fibroblast stromelysin: structure, glycosylation, substrate specificity, and differential expression in normal and tumorigenic cells", Ibid., 84, 6725–29 (1987); Z. Werb et al., Signal transduction through the fibronectin receptor induces collagenase and stromelysin gene expression, J. Cell Biol., 109, 872–889 (1989); L. A. Liotta, C. N. Rao, S. H. Barsky, "Tumor invasion and the extracellular matrix", Lab. Invest., 49, 636–649 (1983); R. Reich, B. Stratford, K. Klein, G. R. Martin, R. A. Mueller, G. C. Fuller, "Inhibitors of collagenase IV and cell adhesion reduce the invasive activity of malignant tumor cells", in Metastasis: Ciba Foundation Symposium; Wiley, Chichester, 1988, pp. 193–210.

Secreted proteinases such as stromelysin, collagenase, and gelatinase play an important role in processes involved in the movement of cells during metastasic tumor invasion. Indeed, there is also evidence that the matrix metalloproteinases are overexpressed in certain metastatic tumor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts isolated from inflammed gingiva: V. J. Uitto, R. Applegren, P. J. Robinson, "Collagenase and neutral metalloproteinase activity in extracts of inflamed human gingiva", J. Periodontal Res., 16, 417–424(1981). Enzyme levels have been correlated to the severity of gum disease: C. M. Overall, O. W. Wiebkin, J. C. Thonard, "Demonstration of tissue collagenase activity in vivo and its relationship to inflammation severity in human gingiva", J. Periodontal Res., 22, 81–88 (1987).

Proteolytic processes have also been observed in the ulceration of the cornea following alkali burns: S. I. Brown, C. A. Weller, H. E. Wasserman, "Collagenolytic activity of alkali-burned corneas", Arch. Opthalmol., 81, 370–373 (1969). Mercapto-containing peptides inhibit the collagenase isolated from alkali-burned rabbit cornea: F. R. Burns, M. S. Stack, R. D. Gray, C. A. Paterson, Invest. Opthalmol., 30, 1569–1575 (1989). Treatment of alkali-burned eyes or eyes exhibiting corneal ulceration as a result of infection with combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine; W. H. Baricos, G. Murphy, Y. Zhou, H. H. Nguyen, S. V. Shah, "Degradation of glomerular basement membrane by purified mammalian metalloproteinases", Biochem. J., 254, 609–612 (1988). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases. Inhibition of this enzyme may alleviate the proteinurea associated with kidney malfunction.

Inhibition of stromelysin activity may prevent the rupturing of atherosclerotic plaques leading to coronary thrombosis. The tearing or rupture of atherosclerotic plaques is the most common event initiating coronary thrombosis. Destabilization and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localized to individual cells in atherosclerotic plaques removed from heart transplant patients at the time of surgery: A. M. Henney, P. R. Wakeley, M. J. Davies,. K. Foster, R. Hembry, G. Murphy, S. Humphries, "Localization of stromelysin gene expression in atherosclerotic plaques by in situ hybridization", Proc. Nat'l. Acad. Sci. U.S.A, 88, 8154–8158 (1991). Inhibition of stromelysin by these compounds may aid in preventing or delaying the degradation of the connective tissue matrix that stabilizes the atherosclerotic plaques, thereby preventing events leading to acute coronary thrombosis.

It is also believed that inhibitors of matrix metalloproteinases would have utility in treating degenerative aortic disease associated with thinning of the medial aortic wall. Aneurysms are often associated with atherosclerosis in this tissue. Increased levels of the degradative activities of the matrix metalloproteinases have been identified in patients with aortic aneurysms and aortic stenosis: N. Vine, J. T. Powell, "Metalloproteinases in degenerative aortic diseases", Clin. Sci., 81, 233–9 (1991). Inhibition of these enzymes may aid in preventing or delaying the degradation of aortic tissue, thus preventing events leading to acute and oftentimes fatal aortic aneurysms.

It is also believed that specific inhibitors of stromelysin and collagenase should be useful as birth control agents. There is evidence that expression of metalloendoproteinases, including stromelysin and collagenase, is observed in unfertilized eggs and zygotes and at further cleavage stages and increased at the blastocyst stage of fetal development and with endoderm differentiation: C. A. Brenner, R. R. Adler, D. A. Rappolee, R. A. Pedersen, Z. Werb, "Genes for extracellular matrix-degrading metalloproteinases and their inhibitor, TIMP, are expressed during early mammalian development", Genes & Develop., 3, 848–59 (1989). By analogy to tumor invasion, a blastocyst may express metalloproteinases in order to penetrate the extracellular matrix of the uterine wall during implantation. Inhibition of stromelysin and collagenase during these early developmental processes should presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation: J. F. Woessner, N. Morioka, C. Zhu, T. Mukaida, T. Butler, W. J. LeMaire "Connective tissue breakdown in ovulation", Steroids, 54, 491–499 (1989). There may also be a role for stromelysin activity during ovulation: C. K. L. Too, G. D. Bryant-Greenwood, F. C. Greenwood, "Relaxin increases the release of plasminogen activator, collagenase, and proteo-glycanase from rat granulosa cells in vitro", Endocrin., 115, 1043–1050 (1984).

Collagenolytic and stromelysin activity have also been observed in dystrophobic epidermolysis bullosa: A. Kronberger, K. J. Valle, A. Z. Eisen, E. A. Bauer, J. Invest. Dermatol., 79, 208–211 (1982); D. Sawamura, T. Sugawara, I. Hashimoto, L. Bruckmer-Tuderman, D. Fujimoto, Y. Okada, N. Utsumi, H. Shikata, Biochem. Biophys. Res. Commun., 174, 1003–8 (1991). Inhibition of metalloendoproteinases should limit the rapid destruction of connective components of the skin.

In addition to extracellular matrix comprising structural components, stromelysin can degrade other in vivo substrates including the inhibitor al-proteinase inhibitor and may therefore influence the activities of other proteinases such as elastase: P. G. Winyard, Z. Zhang, K. Chidwick, D. R. Blake, R. W. Cartell, G. Murphy, "Proteolytic inactivation of human al-antitrypsin by human stromelysin", FEBS Letts., 279, 1, 91–94 (1991). Inhibition of the matrix metalloendoproteinases may potentiate the antiproteinase activity of these endogenous inhibitors.

SUMMARY OF THE INVENTION

The invention encompasses novel N-(mercaptoacyl) peptidyl compounds which are useful inhibitors of matrix metalloendoproteinase-mediated diseases including degenerative diseases (such as defined above) and certain cancers.

DETAILED DESCRIPTION OF THE INVENTION

The invention encompasses an N-(mercaptoacyl)peptidyl compound of formula (I)

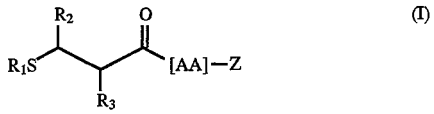

or a pharmaceutically acceptable salt thereof wherein:
$R_1$ is H, $C_{1-6}$alkylmercapto, $C_{2-6}$alkanoyl, $C_{7-11}$aroyl;
$R_2$ is H, $C_{1-6}$alkyl, substituted $C_{1-6}$alkyl wherein the substituent is carboxyl, carboxamido, hydroxyl, sulfonamido;
$R_3$ is $C_{6-10}$aryl $C_{2-3}$alkyl or $C_{6-10}$aryl-substituted $C_{2-3}$alkyl wherein the substituent is $C_{1-3}$alkyl or hydroxy, and wherein the aryl group includes heteroaryl and is selected from the group consisting of:

(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl, and
(27) benzoxazolyl, and mono and di-substituted $C_{6-10}$aryl wherein aryl is as defined above in items (1) to (27) wherein the substituents are independently selected from $C_{1-6}$alkyl, $C_{1-6}$alkyloxy, halo, hydroxy, amino, $C_{1-6}$alkylamino, amino $C_{1-6}$alkyl, carboxyl, carboxyl $C_{1-6}$alkyl, and $C_{1-6}$alkylcarbonyl;
AA is an amino acid radical of formula II

wherein $R_e$ and $R_f$ are individually selected from:
(a) hydrogen,
(b) $C_{1-6}$alkyl,
(c) mercapto $C_{1-6}$alkyl,
(d) hydroxy $C_{1-6}$alkyl, (e) carboxy $C_{1-6}$alkyl,
(f) amino substituted $C_{2-6}$alkyl
(g) aminocarbonyl $C_{1-6}$alkyl,
(h) mono- or di-$C_{1-6}$alkylamino $C_{2-6}$alkyl,
(i) guanidino $C_{2-6}$alkyl,
(j) substituted phenyl $C_{1-6}$alkyl, wherein the substituent is hydrogen, hydroxy, carboxy, $C_{1-4}$ alkyl, or $C_{1-4}$alkyloxy,
(k) substituted indolyl$C_{1-6}$alkyl, wherein the substituent is hydrogen, hydroxy, carboxy, $C_{1-4}$ alkyl, or $C_{1-4}$alkyloxy,
(l) substituted imidazolyl$C_{2-6}$alkyl wherein the substitutent is hydrogen, hydroxy, carboxy, $C_{1-4}$ alkyl, or $C_{1-4}$alkyloxy,
(m) substituted pyridyl$C_{1-6}$alkyl wherein the substitutent is hydrogen, hydroxy, carboxy, $C_{1-4}$ alkyl, or $C_{1-4}$alkyloxy,
(n) substituted pyridylamino$C_{1-6}$alkyl wherein the substituent is hydrogen, hydroxy, carboxy, $C_1$alkyl, or $C_{1-4}$alkyloxy, Z is

wherein $R_5$ and $R_6$ are each
individually selected from the group consisting of:
(a) H,
(b) $C_{1-10}$alkyl,
(c) $C_{6-10}$aryl or $C_{6-10}$aryl $C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl
(26) thiazolyl, and
(27) oxazolyl.

The above amino acids containing radical of formula (II) are intended to be inclusive of all (L)-aminocarboxylic acids such as especially glycine, alanine, valine, leucine, isoleucine, serine, threonine, aspartic acid, asparagine, glutamic acid, glutamine, lysine, hydroxylysine, arginine, homohistidine, phenylalanine, tyrosine, tryptophan, cysteine, methionine, ornithine, homoserine, and citrulline.

One preferred group of compounds are those in which in formula (I), $R_1$ is hydrogen, acetyl or benzoyl, $R_2$ is hydrogen or methyl, $R_3$ is 2-phenylethyl or 2-[4-($C_{1-3}$alkyl)phenyl]ethyl [AA] is an L-amino acid, Z is a residue of β-alanine, L-alanine, glycine and aniline. By "residue of" is meant the group attached to the amino nitrogen. Especially preferred are the following compounds:

(1a) N-(2-thiomethyl-4-phenylbutanoyl)-(L)-leucinamide;

(1b) N-(2-thiomethyl-4-phenylbutanoyl)-(L)-leucine, N-phenylamide;

(1c) N-(2-thiomethyl-4-phenylbutanoyl)-(L)-leucine, N-benzylamide;

(1d) N-(2-thiomethyl-4-phenylbutanoyl)-(L)-leucine, N-(2-phenylethyl)amide;

(1e) N-(2-thiomethyl-4-phenylbutanoyl)-(L)-phenylalaninamide;

(1f) N-(2-thiomethyl-4-phenylbutanoyl)-(L)-phenylalanine, N-phenylamide;

(1g) N-(2-thiomethyl-4-phenylbutanoyl)-(L)-phenylalanine, N-benzylamide;

(1h) N-(2-thiomethyl-4-phenylbutanoyl)-(L)-phenylalanine-b-alanine;

This invention also concerns pharmaceutical composition and method of inhibiting lytic activity of metalloendoproteinase, particularly in the treatment of matrix metalloendoproteinase-mediated or implicated disorders or diseases in a patient (which is defined to include man and/or mammalian animals raised in the dairy, meat, or fur industries or as pets) in need of such treatment comprising administering a metalloendoproteinase inhibitor of formula (I) as the active constituent.

Thus, this invention concerns pharmaceutical compositions and methods of inhibiting lytic activity of stromelysin, particularly in the treatment of stromelysin mediated or implicated disorders or diseases in a patient in need of such treatment comprising administering a stromelysin inhibitor of formula (I) as the active constituent.

This invention also concerns pharmaceutical compositions and methods of inhibiting the lytic activity of collagenase particularly in the treatment of collagenase mediated or implicated disorders or diseases in patients in need of such treatment comprising administering a collagenase inhibitor of formula (I) as the active constituent.

This invention further concerns pharmaceutical compositions and methods of inhibiting the lytic activity of gelatinase, particularly in the treatment of gelatinase-mediated or implicated disorders or diseases in a patient in need of such treatment comprising administering a gelatinase inhibitor of formula (I) as the active constituent.

Moreover the invention also encompasses compositions, treatment, and method for co-administration of a compound of formula (I) with a PMN elastase inhibitor such as those described in EP 0 337 549, published on Oct. 18, 1989.

Compounds of the instant invention are conveniently prepared using the procedures described generally below in the flow diagram and more explicitly described in the working examples. Unless otherwise specifically noted, substantially equimolar amounts of the reactants are employed, and reagents are employed in slight excess. The preferred reaction conditions are as noted in the flow diagram. These conditions may be modified in a manner well known in the art.

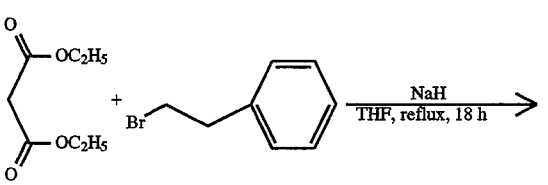

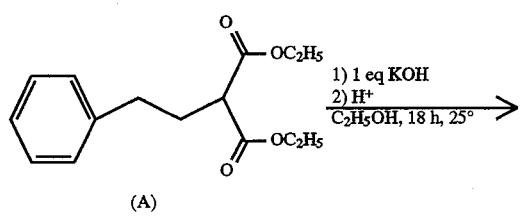

(A)

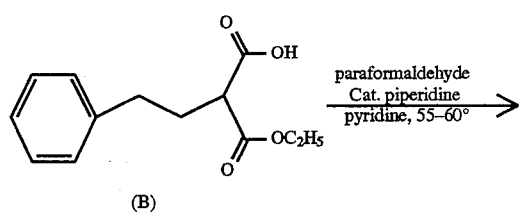

(B)

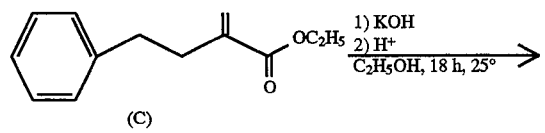

(C)

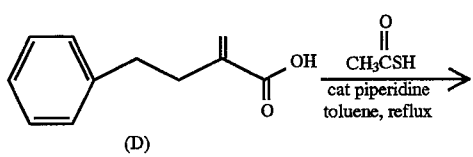

(D)

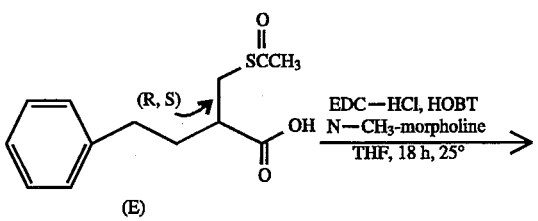

(E)

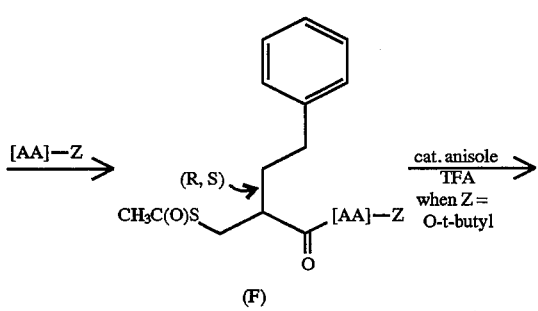

(F)

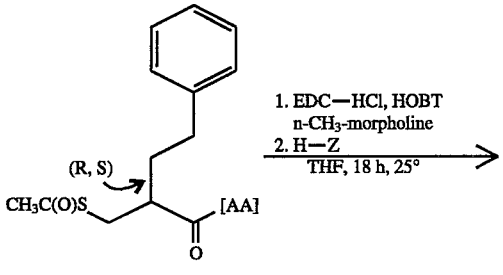

(G)

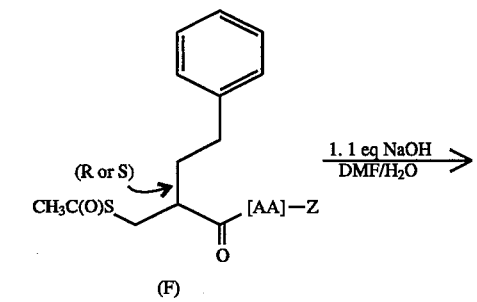

(F)

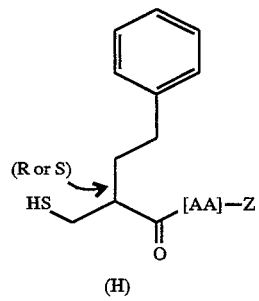

(H)

The flow diagram shows that diethyl malonate is monoalkylated with 2-phenylethyl bromide to form. diester (A). The monoacid monoester (B) is formed from (A) by treatment with one equivalent of potassium hydroxide. Treatment of (B) under Mannich-like conditions with paraformaldehyde in the presence of piperidine produces substituted acrylate ester (C). Basic hydrolysis forms the acrylic acid (D). Thioacetic acid added to the double bond of (D) to form (E). Standard peptide bond forming conditions 1-(3-dimethylaminopropyl)-3-ethylcarbodiimide·hydrochloride (EDC)-HCl, N-hydroxybenzotriazole (HOBT), N-methyl-morpholine) of (E) with a derivatized amino acids ([AA]-Z) produces (F) as a mixture of diastereomers which are separated by column chromatography. Alternatively, when X=O-t-butyl, treatment with trifluoroacetic acid in the presence of anisole results in free acid (G). Standard peptide bond forming conditions (water soluble carbodiimide, N-hydroxybenzotriazole, N-methyl-morpholine) of (G) with H-Z forms (F). Basic hydrolysis of the thioester in (F) produces the free mercapto compound (H).

The usefulness of the compounds as inhibitors for matrix metalloendoproteinases are determined through assays for the specific enzymes as described hereafter.

A representative number of compounds of the instant invention of the formula (I) are shown below in Table 1 to exhibit in vitro inhibitory activities with respect to stromelysin. In particular, the compounds of formula (I) have been shown to inhibit the hydrolysis of substance P, (that is, Arg-Pro-Lys-Pro-Gln-Gln-Phe-Phe-Gly-Leu-Met-NH$_2$) by stromelysin employing the method described in detail in the literature: R. Harrison, J. Teahan, R. Stein, "A semicontinuous, high-performance liquid chromatography-based assay for stromelysin", Analytical Biochem, 180, 110–113 (1989).

TABLE 1

INHIBITION OF STROMELYSIN
BY MERCAPTOACYL PEPTIDES

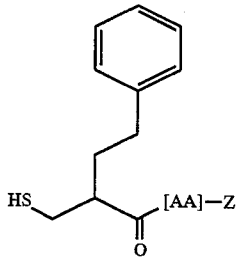

| | | | IC$_{50}$ ± S.E.[a] (µM) | |
|---|---|---|---|---|
| Compd. No. | [AA] | Z | Higher Rf isomer | Lower Rf isomer |
| (1a) | (L)-Leu | NH$_2$ | 3.3 ± 0.4 | 0.96 ± 0.1 |
| (1b) | (L)-Leu | NHPh | 1.6 ± 0.5 | 0.49 ± 0.1 |
| (1c) | (L)-Leu | NHCH$_2$Ph | 7.3 ± 3.3 | 2.5 ± 1.2 |
| (1d) | (L)-Leu | NH(CH$_2$)$_2$Ph | 5.0 ± 1.0 | 3.7 ± 1.9 |
| (1e) | (L)-Phe | NH$_2$ | 3.1 ± 0.5 | 1.9 ± 0.6 |
| (1f) | (L)-Phe | NHPh | 1.1 ± 0.3 | 2.2 ± 0.8 |
| (1g) | (L)-Phe | NHCH$_2$Ph | 63% inh. @ 1.4 µM | 98% inh. @ 3.3 µM |
| (1h) | (L)-Phe | NH(CH$_2$)$_2$CO$_2$H | 4.1 ± 0.35 | |

[a]S.E. = standard error.
[b]Ph = phenyl

The activity of the compounds as collagenase inhibitor may be determined using the procedure of Cawston and Barrett, Anal. Biochem. 99. 340–345 (1979) whereby 1 mM of the inhibitor being tested or dilutions thereof are incubated at 37° C. overnight (about 16 hours) with native collagen and collagenase (buffered with Tris HCl-CaCl$_2$; pH 7.6). The collagen is acetyl $^{14}$C collagen. The samples are centrifuged to sediment undigested collagen and an aliquot of the radioactive supernatant removed for assay on a scintillation counter as a measure of hydrolysis. The collagenase activity in the presence of 1 mM inhibitor, or a dilution thereof is compared to activity in a control devoid of inhibitor and the results reported as inhibitor concentration effecting 50% inhibition of collagenase.

This invention also relates to a method of treatment for patients (including man and/or mammalian animals raised in the dairy, meat, or fur industries or as pets) suffering from disorders or diseases which can be attributed to stromelysin as previously described, and more specifically, a method of treatment involving the administration of the matrix metalloendoproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloendoproteinases such as found in certain metastatic tumor cell lines.

For the treatment of rheumatoid arthritis, osteoarthritis, and in diseases and indications resulting from the over-expression of matrix metalloendoproteinases such as found in certain metastatic tumor cell lines or other diseases mediated by the matrix metalloendoproteinases, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above- indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

EXAMPLE 1

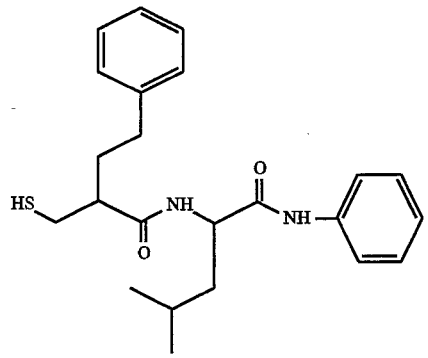

Diethyl 2-[2-(phenyl)ethyl]malonate

According to the described procedure (J. Med Chem. 1984, 27, 967–978), to a 2 liter 3-neck round bottom flask was attached a pressure equalized addition funnel and a water cooled reflux condenser. A large Teflon coated magnetic stirring bar was added and the flask flamed dried under nitrogen. Sodium hydride (60% in mineral oil, 42 g, 1.06 moles) was added to the flask and the mineral oil removed by washing the solid three times with 40 mL of hexane. One liter of dry tetrahydrofuran (THF) (distilled over potassium/benzophenone) was added to the flask under nitrogen. A mineral oil bubbler was attached by a rubber septum to the flask and diethyl malonate was added dropwise over 1 h, keeping the temperature <18° C. When hydrogen evolution had ceased, 197.5 g of 1-bromoethyl benzene (1.06 mole) was added dropwise over 30 minutes with cooling (<30°). The solution was gently refluxed overnight. The mixture was cooled to room temperature and poured into 200 mL of ice water containing 150 mmole of HCl and stirred 5 minutes. The organic layer was separated and the aqueous layer extracted with 3×100 mL of ether. The organic layers were combined and washed with 2×100 mL of saturated sodium bicarbonate and 1×100 mL of brine. The solution was dried over anhydrous MgSO$_4$. The ether was removed under reduced pressure and the product distilled under vacuum (bp=146–148@1.5 mm Hg). Recovered 203 g of product (yield=72%).

$^1$H-NMR (CDCl$_3$, 200 mHz, d, ppm,) 7.4–7.2 (m, 5H), 4.3–4.16 (q, 4H), 3.4–3.3 (t, 1H), 2.74–2.64 (t, 2H), 2.32–2.18 (q, 2H), 1.36–1.26 (t, 6H).

Monoethyl 2-[2-(phenyl)ethyl]malonic acid,

Following the reported procedure (J. Med Chem. 1982, 25, 109–113), diethyl 2-[2-(phenyl)ethyl]-malonate (200 g, 0.756 mole) was dissolved in 600 mL of absolute ethanol in a 2 liter round bottomed flask fitted with a Teflon coated stirring bar. The solution was cooled to 5° C. in an ice bath. Then 49.9 g of potassium hydroxide (85%) in 600 mL of absolute ethanol was added dropwise to the rapidly stirring solution over a 2 h period with the solution temperature kept under 15° C. The solution was stirred under nitrogen overnight at 25° C. Ethanol was removed under reduced pressure and the syrupy residue dissolved in 800 mL of ice water. The solution was washed with 2×200 ml of ether, the aqueous layer acidified with concentrated HCl (pH<3) and extracted 3×300 mL of ether. The combined ether layer was washed with brine and dried over anhydrous MgSO$_4$. The solution was filtered and the ether removed under reduced pressure to give a clear oil. Recovered 162 g of product (90% yield).

$^1$H-NMR (CDCl3 , 200 mHz, δ, ppm,) 7.4–7.2 (m, 5H), 4.3–4.16 (q, 2H), 3.5–3.4 (t, 1H), 2.78–2.68 (t, 2H), 2.36–2.2 (q, 2H), 1.36–1.26 (t, 3H).

2-Methylene-4-phenylbutyric acid, ethyl ester

Monoethyl 2-[2-(phenyl)ethyl]malonic acid (47.2 g, 200 mole) was added to 40 mL of pyridine in a 250 mL round bottomed flask fitted with a Teflon coated stirring bar. Piperidine (3 mL) and paraformaldehyde (8.4 g, 280 mmole) were added to the flask and the flask was heated to 55°–60° C. until gas evolution ceased. TLC indicated that no starting material remained. The solution was worked up by removing the solvent under reduced pressure. Water (50 mL ) and enough 12N HCl was added to the flask to acidify the mixture (pH<3). The mixture was extracted with ether (3×50 mL) and back extracted with brine. The solution was dried over MgSO$_4$ and filtered. The reaction mixture was shown to be clean by NMR and TLC and used without further purification. Recovered 36.3 g material (89% yield).

$^1$H-NMR (CDCl$_3$, 200 mHz, δ, ppm,) 7.4–7.2 (m, 5H), 6.18 (d, 1H), 5.52 (d, 1H), 4.3–4.16 (q, 2H), 2.86–2.74 (t, 2H), 2.78–2.68 (t, 2H), 1.36–1.26 (t, 3H).

2-Methylene-4-phenylbutyric acid

4-Phenyl-2-methylenebutyric acid, ethyl ester (10 g, 49 mmole) was dissolved in 100 mL of absolute ethanol. Potassium hydroxide (3.32 g, 85%, 50 mmole) was added to the solution and the solution stirred overnight at room temperature. After 18 h, all of the ester was hydrolyzed. The solvent was removed under reduced pressure and the syrup dissolved in water. Enough concentrated HCl was added to acidify the solution (pH<3) and the product was extracted with ether (3×50 mL). The solution was dried over MgSO$_4$, filtered and the solvent removed under reduced pressure. Recovered 8.6 g of product (97% yield).

$^1$H-NMR (CDCl$_3$, 200 mHz, δ, ppm,) 7.4–7.2 (m, 5H), 6.30 (d, 1H), 5.62 (d, 1H), 2.86–2.74 (t, 2H), 2.78–2.68 (m, 2H).

2-[Acetylthiomethyl]-4-phenylbutyric acid

A 250 mL round bottomed flask, fitted with a Teflon magnetic stirring bar and a reflux condenser, was filled with 150 mL of toluene, 0.5 mL piperidine and 8.6 g (49 mmol) of 4-phenyl-2-methylenebutyric acid. Then 4.1 g (54 mmole) of thiolacetic acid was added to the solution and the mixture heated to reflux for 8 h under nitrogen. $^1$H-NMR analysis of the reaction mixture indicated some starting material remained. Another 1 g of thiolacetic acid was added and the mixture stirred at reflux for an additional 4 hours. By $^1$H-NMR, all of the starting material was seen to have reacted. The solution was cooled to 5° C. and 100 mL of ether added to the mixture. The excess thiolacetic acid was removed by extraction (3×50 mL 2% sodium bicarbonate). Then 50 ml of 1N HCl was added to the organic layer and the solution shaken vigorously. The organic layer was separated and dried over MgSO$_4$. The solution was filtered and the solvent removed under reduced pressure. Recovered 10.0 g of product (81% yield).

$^1$H-NMR (CDCl$_3$, 200 mHz, δ, ppm,) 7.4–7.2 (m, 5H), 3.18 (d, 1H), 3.12 (d, 1H), 2.7–2.6 (m, 3H), 2.30 (s, 3H), 2.1–1.9 (m, 2H).

N-(2-Acetylthiomethyl-4-phenylbutanoyl)-(L)-leucine t-butyl ester

To a solution of 4-phenyl-2-[acetylthio-methyl]butyric acid (3.57 g. 14.2 mmole) in 66 mL of THF at 0° C. was added (S)-leucine, t-butyl ester (2.91 g 15.6 mmole) and 1-hydroxybenzotriazole hydrate (HOBT·H$_2$O, 2.86 g, 21.2 mmole) and N-methylmorpholine (4.29 g, 42.4 mmole). The mixture was stirred at 0° C. for 15 minutes, then 5.42 g of 1-ethyl-3-(3-dimethyl-aminopropyl) carbodiimide hydrochloride (EDC·HCl, 28.3 mmole) was added and the mixture stirred overnight. The solution was worked up by adding 100 mL methylene chloride and the mixture extracted with 3×50 ml of 5% sodium bicarbonate and washed with 2×50 mL of brine. The organic layer was dried over MgSO$_4$, filtered, and the solvent removed under reduced pressure. The residue was purified by flash column chromatography on silica gel eluted with methylene chloride/ethyl acetate (95/5).

The product was separated as diastereomeric (R,S) and (S,S) fractions. The absolute stereochemistry of each fraction was not determined. Higher R$_f$ material =1.78 g; lower R$_f$ material =1.90 g. Higher R$_f$ fraction $^1$H-NMR (CDCl$_3$, 200 mHz, δ, ppm,) 7.3–7.2 (m, 5H), 5.9 (bd, 1H), 4.56 (dd, 1H), 3.06 (d, 2H), 2.73–2.58 (bm, 2H), 2.33 (s, 3H), 2.2–1.5 (m, 6H), 1.5 (s, 9H), 0.96 (d, 6H).

Lower R$_f$ fraction $^1$H-NMR (CDCl$_3$, 200 mHz, δ, ppm,) 7.3–7.2 (m, 5H), 5.98 (bd, 1H), 4.56 (dd, 1H), 3.08 (dd, 2H), 2.73–2.58 (bm, 2H), 2.33 (s, 3H), 2.2–1.5 (m, 6H), 1.5 (s, 9H), 0.96 (d, 6H).

N-(2-Acetylthiomethyl-4-phenylbutanoyl)-(L)-leucine

The higher R$_f$ TLC fraction product of N-(2-acetylthiomethyl-4-phenylbutanoyl)-(L)-leucine, t-butyl ester (1.90 g, 4.5 mmole) was dissolved in 5 mL of trifluoroacetic acid (TFA) and 420 mg anisole at 0° C. for 18 h. No starting material was observed by TLC. The TFA was azeotroped off under reduced pressure with benzene. The product was suspended in hexane and filtered to remove the anisole. Recovered 1.2 g of N-(2-acetylthiomethyl-4-phenylbutanoyl)-(L)-leucine (73% yield).

$^1$H-NMR (CDCl$_3$, 200 mHz, δ, ppm), 7.3–7.1 (m, 5H), 6.1 (bd, 1H), 4.68 (m, 1H), 3.06 (d, 2H), 2.73–2.58 (bm, 2H), 2.33 (s, 3H), 2.2–1.5 (m, 6H), 0.96 (d, 6H).

N- (2-Acetylthiomethyl-4-phenylbutanoyl)-(L)-leucine, N-phenylamide

To a solution of N-(2-acetylthiomethyl-4-phenylbutanoyl) -(L)-leucine (derived from the higher R$_f$ TLC fraction) (182 mg. 0.5 mmole) in 2 mL of THF at 0° C. was added aniline (93 mg, 1.0 mmole) and 1-hydroxybenzotriazole hydrate (HOBT·H$_2$O, 101 mg, 0.75 mole) and N-methylmorpholine (202 mg, 2.0 mmole). The mixture was stirred at 0° C. for 15 minutes, then 192 mg of 1-ethyl-3-(3- dimethylaminopropyl)carbodiimide hydrochloride (EDC·HCl, 1.0 mmole) was added and the mixture stirred overnight. The solution was worked up by adding 7 mL methylene chloride and the mixture extracted with 3×3 ml of 5% sodium bicarbonate, then 2×2 mL of brine. The organic layer was dried over $MgSO_4$, filtered and the solvent removed under reduced pressure. The residue was purified by flash column chromatography on silica gel eluted with methylene chloride/ethyl acetate (90/10) to obtain 110 mg of product (yield =50%). By $^1$H-NMR, we see two rotomers present at room temperature.

$^1$H-NMR (CDCl$_3$, 200 mHz, δ, ppm), 8.50 (bd 1H), 7.55 (dd, 2H), 7.4–7.0 (m, 8H), 6.1 (bd, 1H), 4.68 (m, 1H), 3.06 (2d, 2H), 2.73–2.58 (bm, 2H), [2.2, 2.0 (s, 3H)], 2.5–1.6 (m, 6H), 0.98 (d, 6H).

N-(2-Thiomethyl-4-phenylbutanoyl)-(L)-leucine, N-phenylamide (1b, higher Rf isomer)

To a solution of N-(2-acetylthiomethyl-4-phenylbutanoyl)-(L)-leucine, N-phenylamide (derived from the higher $R_f$ TLC fraction) (60 mg, 0.136 mmole), 250 μL dimethylformamide and 75 μL of water in a 1 mL spin vane vial under nitrogen was added 7.2 μl of 5N NaOH. The solution was stirred at 25° C. overnight. Workup consisted of syringing the solution into 10 mL of degassed water containing 0.25 mL glacial acetic acid. A precipitate formed, was filtered and washed with 2×1 ml of cold water. The product was dried under high vacuum at 55° C. overnight. Recovered 29 mg of product (yield=54%).

MS: m/z 399 (M+1)$^+$; $^1$H-NMR (CDCl$_3$, 200 mHz, δ, ppm), 8.60 (s, 1H), 7.55 (dd, 2H), 7.4–7.0 (m, 8H), 6.25 (bd, 1H), 4.72 (m, 1H), 2.80 (m, 2H), 2.73–2.58 (bm, 2H), (2.3, m 1H), 2.2–1.5 (m, 6H), 0.98 (d, 6H).

Anal. Calcd. for $C_{23}H_{30}N_2O_2S$: C, 69.31; H, 7.59; N, 7.03. Found: C, 69.23; H, 7.50; N, 6.93.

The following additional compounds were prepared according to the method described in Example 1.

EXAMPLE 2

N-(2-Thiomethyl-4-phenylbutanoyl)-(L)-leucine, N-phenylamide (1b, lower $R_f$ isomer)

MS: m/z 399 (M+1)$^+$; $^1$H-NMR (CDCl$_3$, 200 mHz, δ, ppm), 8.65 (s, 1H), 7.55 (dd, 2H), 7.4–7.0 (m, 8H), 6.25 (bd, 1H), 4.72 (m, 1H), 2.80 (m, 2H), 2.73–2.58 (bm, 2H), 2.2 (m 1H), 2.2–1.5 (m, 6H), 0.96 (d, 6H).

Anal. Calcd. for $C_{23}H_{30}N_2O_2S$: C, 69.31; H, 7.59; N, 7.03. Found: C, 69.70; H, 7.75; N, 6.88.

EXAMPLE 3

N-(2-Thiomethyl-4-phenylbutanoyl)-(L)-leucinamide, (1a, higher $R_f$ isomer)

MS: m/z 323 (M+1)$^+$; $^1$H-NMR (CDCl$_3$, 200 mHz, δ, ppm), 7.36–7.1 (m, 5H), 6.25 (bs, 1H), 6.1 (d, 1H), 5.55 (bs, 1H), 4.60 (m, 1H), 2.80 (m, 2H), 2.73–2.50 (bm, 3H), 2.3 (m, 1H), 2.2–1.6 (m, 4H), 1.48 (t, 1H), 0.96 (dd, 6H).

EXAMPLE 4

N-(2-Thiomethyl-4-phenylbutanoyl)-(L)-leucinamide, (1a, lower $R_f$ isomer)

MS: m/z 323 (M+1)$^+$; $^1$H-NMR (CDCl$_3$, 200 mHz, δ, ppm), 7.36–7.1 (m, 5H), 6.45 (bs, 1H), 6.1 (bd, H), 5.55 (bs, 1H), 4.60 (m, 1064 1H), 2.80 (m, 2H), 2.73–2.50 (bm, 3H), 2.3 (m, 1H), 2.2–1.4 (m, 5H), 0.96 (dd, 6H).

Anal. Calcd. for $C_{17}H_{26}N_2O_2S$: C, 63.32 H, 8.13; N, 8.69. Found: C, 63.52; H, 7.92; N, 8.45.

EXAMPLE 5

N-(2-Thiomethyl-4-phenylbutanoyl)-(L)-leucine, N-benzylamide (1c, higher $R_f$ isomer)

MS: m/z 413 (M+1)$^+$; $^1$H-NMR (CDCl$_3$, 200 mMz, δ, ppm), 7.26–7.20 (m, 8H), 7.14 (dd, 2H), 6.56 (bs, 1H), 6.04 (bd, 1H), 4.58 (m, 1H), 4.48 (d, 2H), 2.90–2.72 (m, 2H), 2.64–2.40 (m, 2H), 2.24 (m, 1H), 2.0–1.6 (m, 4H), 1.48 (t, 1H), 0.96 (d, 6H).

Anal. Calcd. for $C_{24}H_{32}N_2O_2S$: C 69.87; H, 7.82; N, 6.79. Found: C, 69.99; H, 7.70; N, 6.59.

EXAMPLE 6

N-(2-Thiomethyl-4-phenylbutanoyl)-(L)-leucine, N-benzylamide (1c, lower $R_f$ isomer)

MS: m/z 413 (M+1)$^+$; $^1$H-NMR (CDCl$_3$, 200 mHz, δ, ppm), 7.26–7.20 <m , 8H), 7.14 (dd, 2H), 6.78 (bs, 1H), 5.96 (bs, 1H), 4 .60 (m, 1H), 4.44 (d, 2H), 2.80–2.62 (m, 4H), 2. 24 (m, 1H), 2.0 (m, 1H), 1.9–1.5 (m, 3H), 1.48 (t, 1H), 0.96 (d, 6H).

Anal. Calcd. for $C_{24}H_{32}N_2O_2S$: C, 69.87 H, 7.82; N, 6.79. Found: C, 69.67; H, 7.58; N, 6.58.

EXAMPLE 7

N-(2-Thiomethyl-4-phenylbutanoyl)-(L)-leucine, N-(2-phenylethyl) amide (1d, higher $R_f$ isomer)

MS: m/z 427 (M+1)$^+$; $^1$H-NMR (CDCl$_3$, 200 mHz, δ, ppm), 7.36–7.1 (m, 10H), 6.10 (bs, 1H), 6.05 (d, 1H), 4.50 (m, 1H), 3.50 (m, 2H), 2.80 (t, 2H), 2.7–2.60 (m, 2H), 2.25 (m, 1H), 2.0 (m, 2H), 1.60 (m, 3H), 1.48 (t, 1H), 0.96 (dd, 6H).

Anal. Calcd. for $C_{25}H_{34}N_2O_2S$: C, 65.46; H, 6.11; N, 7.47. Found: C, 65.79; H, 6.00; N, 7.49.

EXAMPLE 8

N-(2-Thiomethyl-4-phenylbutanoyl)-(L)-1 eucine, N-(2-phenylethyl) amide (1d. lower $R_f$ isomer)

MS: m/z 427 (M+1)$^+$; $^1$H-NMR (CDCl$_3$, 200 mHz, δ, ppm), 7.36–7.1 (m, 10H), 6.50 (bs, 1H), 6.05 (d, 1H), 4.50 (m, 1H), 3.50 (m, 2H), 2.80 (t, 2H), 2.7–2.50 (m, 4H), 2.25 (m, 1H), 2.0 (m, 1H), 1.9–1.5 (m, 2H), 1.48 (t, 1H), 0.96 (dd, 6H).

Anal. Calcd. for $C_{25}H_{34}N_2O_2S$: C, 65.46; H, 6.11; N, 7.47. Found: C, 65.69; H, 5.90; N, 7.50.

EXAMPLE 9

N-(2-Thiomethyl-4-phenylbutanoyl)-(L)-phenylalaninamide (1e, higher $R_{f\ isomer}$)

MS: m/z 357 (M$^+$); $^1$H-NMR: (CDCl$_3$, 200 mHz, δ, ppm), 7.27 (m, 8H), 7.16 (d, 2H), 6.28 (d, 1H), 5.85 (s, 1H), 5.43 (s, 1H), 4.79 (dd, 1H), 2.56 (dd, 2H), 3.12 (dd, 2H), 2.69 (m, 2H), 2.25 (m, 1H), 1.90 (m, 2H). Anal. Calcd. for $C_{20}H_{24}N_2O_2S$: C, 67.39; H, 6.79; N, 7.86. Found: C, 67.69; H, 7.14; N, 7.12.

EXAMPLE 10

N-(2-Thiomethyl-4-phenylbutanoyl)-(L)-phenylalaninamide (1e, lower $R_f$ isomer)

MS: m/z 357 (M$^+$); $^1$H-NMR: (CDCl$_3$, 200 mHz, δ, ppm), 7.23 (m, 8H,), 7.01 (d, 2H), 6.27 (s, 1H), 6.20 (d, 1H), 5.50 (s, 1H), 4.84 (dd, 1H), 4.69 (m, 1H), 3.26 (dd, 2H), 3.12 (dd, 2H), 2.70 (m, 2H), 2.20 (m, 1H), 1.82 (m, 2H).

Anal. Calcd. for $C_{20}H_{24}N_2O_2S$: C, 67.39; H, 6.79; N, 7.86. Found: C, 67.20; H, 6.59; N, 7.57.

EXAMPLE 11

N-(2-Thiomethyl-4-phenylbutanoyl)-(L)-phenylalanine, N-phenylamide (1f, higher R_f isomer)

MS: m/z 433 (M⁺); $^1$H-NMR: (CDCl$_3$, 200 mHz, δ, ppm) 7.99 (s, 1H), 7.46–6.94 (m, 15H), 6.26 (d, 1H), 4.88 (dd, 1H), 3.20 (dd, 2H), 3.16 (dd,2H), 2.69 (m, 2H), 2.12 (m, 1H), 1.82 (m, 2H). Anal. Calcd. for $C_{26}H_{28}N_2O_2S$-0.20 H20: C, 71.59; H, 6.56; N, 6.42. Found: C, 71.60; H, 6.60; N, 6.22.

EXAMPLE 12

N-(2-Thiomethyl-4-phenylbutanoyl)-(L)-phenylalanine, N-phenylamide (1f, lower R_f isomer)

MS: m/z 433 (M⁺); $^1$H-NMR: (CDCl$_3$, 200 mHz, δ, ppm), 8.36 (s, 1H), 7.46–6.94 (m, 15H), 6.43 (d, 1H), 5.03 (dd, 1H), 3.26 (dd, 2H), 3.16 (dd, 2H), 3.16 (dd, 2H), 2.69 (m, 2H), 2.25 (m, 1H) 1.84 (m, 2H).

Anal. calcd. for $C_{26}H_{28}N_2O_2S$: C, 72.19; H, 6.52; N, 6.48. Found: C, 71.81; H, 6.44; N, 6.31.

EXAMPLE 13

N-(2-Thiomethyl-4-phenylbutanoyl)-(L)-phenylalanine, N-benzylamide (1 g, higher Rf isomer)

MS: m/z 447 (M⁺); $^1$-NMR: (CDCl$_3$, 200 mHz, δ, ppm), 7.34–7.19 (m, 13H), 7.10 (dd, 2E), 6.23 (d, 1H), 6.06 (d, 1H), 4.72 (dd, 1E), 4.38 (d, 2H), 3.15 (dd, 2H), 2.50 (dd, 2H), 2.66 (m, 2H), 2.22 (m, 1H), 1.84 (m, 2H).

Anal. Calcd. for $C_{27}H_{30}N_2O_2S$: C, 72.61; H, 6.77; N, 6.27. Found: C, 72.48; H, 6.77; N. 6.08.

EXAMPLE 14

N-(2-Thiomethyl-4-phenylbutanoyl)-(L)-phenylalanine, N-benzylamide (1g, lower Rf isomer)

MS: m/z 447 (M⁺); 1H-NMR: (CDCl$_3$, 200 mHz, δ, ppm), 7.35–7.09 (m, 13E), 7.01 (dd, 2H) 6.72 (t, 1H), 6.26 (d, 1H), 4.90 (dd, 1H), 4.36 (d, 2H), 3.18 (dd, 2H), 2.32 (dd, 2H), 2.62 (m, 2H), 2.16 (m, 1H), 1.80 (m, 2H).

Anal. Calcd. for $C_{27}H_{30}N_2O_2S$: C, 72.61; H, 6.77; N, 6.27. Found: C, 72.78; H, 6.77; N, 6.30.

EXAMPLE 15

N-(2-Thiomethyl-4-phenylbutanoyl)-(L)-phenylalanine-β-alanine (1h, higher Rf isomer)

MS: m/z 429 (M⁺); $^1$H-NMR: (CDCl$_3$, 200 mHz, δ, ppm), 7.36–7.06 (m, 10H), 5.07 (dd, 1H), 3.44 (m, 2H), 3.07 (dd, 2H), 2.50 (dd, 2H), 2.64 (m, 2H), 2.22 (m, 1H), 2.30 (t, 2H), 1.82 (m, 2H).

What is claimed is:

1. A compound of formula I

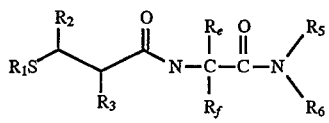

wherein R$_1$ is hydrogen, acetyl or benzoyl,

R$_2$ is hydrogen or methyl,

R$_3$ is 2-phenylethyl or 2-[4-($C_{1-3}$alkyl)phenyl]ethyl,

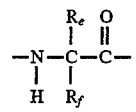

is an L-amino acid,

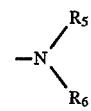

is a residue of β-alanine, L-alanine, glycine and aniline.

2. A compound according to claim 1 selected from the group consisting of:

(a) N-(2-thiomethyl-4-phenylbutanoyl)-(L)-leucinamide;

(b) N-(2-thiomethyl-4-phenylbutanoyl)-(L)-leucine, N-penylamide;

(c) N-(2-thiomethyl-4-phenylbutanoyl)-(L)-leucine, N-benzylamide;

(d) N-(2-thiomethyl-4-phenylbutanoyl)-(L)-leucine, N-(2-phenylethyl)amide;

(e) N-(2-thiomethyl-4-phenylbutanoyl)-(L)-phenylalaninamide;

(f) N-(2-thiomethyl -4-phenylbutanoyl)-(L)-phenylalanine, N-phenylamide;

(g) N-(2-thiomethyl-4-phenylbutanoyl)-(L)-phenylalanine, N-benzylamide;

(h) N-(2-thiomethyl-4-phenylbutanoyl)-(L)-phenylalanine-b-alanine.

3. A composition useful for inhibiting the lytic activity of matrix metalloendoproteinases comprising a lysis inhibiting amount of a compound of claim 1 in admixture with a pharmaceutically acceptable carrier.

4. A composition in unit dose form useful for inhibiting the lytic activity of matrix metalloendoproteinases comprising from about 1 mg to about 500 mg of the compound of claim 1 and a pharmaceutically acceptable carrier.

5. A compound of formula I

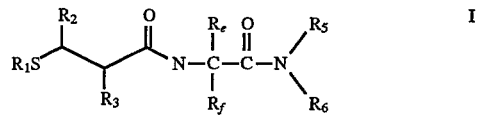

or a pharmaceutically acceptable salt thereof wherein:

R$_1$ is H, $C_{1-6}$alkylmercapto, $C_{2-6}$alkanoyl, $C_{7-11}$aroyl:

R$_2$ is H, $C_{1-6}$alkyl, substituted $C_{1-6}$alkyl wherein the substituent is carboxyl, carboxamido, hydroxy, sulfonamide;

R$_3$ is $C_{6-10}$aryl$C_{2-3}$alkyl or $C_{6-10}$aryl substituted $C_{2-3}$alkyl wherein the substituent is $C_{1-3}$alkyl or hydroxy, and wherein the aryl group is selected from the group consisting of:

(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,

(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl
(26) benzthiazolyl, and
(27) benzoxazolyl, and mono and di-substituted $C_{6-10}$aryl as defined above in items (1) to (27) wherein the substituents are independently selected from $C_{1-6}$alkyl, $C_{1-6}$alkaloxy, halo, hydroxy, amino, $C_{1-6}$alkylamino, amino$C_{1-6}$alkyl, carboxyl, $C_{1-6}$alkyl, and $C_{1-6}$alkylcarbonyl;

$R_e$ and $R_f$ are individually selected from:
(a) hydrogen
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{2-6}$alkyl,
(g) aminocarbonyl $C_{1-6}$alkyl,
(h) mono- or di-$C_{1-6}$alkylamino $C_{2-6}$alkyl,
(i) guanidino $C_{2-6}$alkyl,
(j) substituted phenyl$C_{1-6}$alkyl, wherein the substituent is hydrogen, hydroxy, carboxy, $C_{1-4}$alkyl, or $C_{1-4}$alkyloxy,
(k) substituted indolyl$C_{1-6}$alkyl, wherein the substituent is hydrogen, hydroxy, carboxy, $C_{1-4}$alkyl, or $C_{1-4}$alkyloxy,
(l) substituted imidazolyl$C_{2-6}$alkyl wherein the substituent is hydrogen, hydroxy, carboxy, $C_{1-4}$alkyl, or $C_{1-4}$alkyloxy,
(m) substituted pyridyl$C_{1-6}$alkyl wherein the substituent is hydrogen, hydroxy, carboxy, $C_{1-4}$alkyl, or $C_{1-4}$alkyloxy,
(n) substituted pyridylamino$C_{1-6}$alkyl wherein the substituent is hydrogen, hydroxy, carboxy, $C_{1-4}$alkyl, or $C_{1-4}$alkyloxy;

$R_5$ is selected from the group consisting of:
(a) H,
(b) $C_{1-10}$alkyl, $R_6$ is selected from the group consisting of:
(a) carboxy $C_{1-2}$alkyl, and
(b) $C_{6-10}$aryl wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl, and
(27) oxazolyl.

6. A compound which is N-(2-thiomethyl-4-phenylbutanoyl)-(L)-leucine, N-benzylamide, or a pharmaceutical acceptable salt thereof.

7. A composition useful for inhibiting the lytic activity of matrix metalloendoproteinases comprising a lysis inhibiting amount of a compound of claim 6 in admixture with a pharmaceutically acceptable carrier.

8. A method for inhibiting the lytic activity of metalloendoproteinases comprising administering to a subject suffering from matrix metalloendoproteinase mediated disease, an inhibitory amount of the compound of claim 1.

9. A method according to claim 8 in which the metalloendoproteinases is stromelysin.

10. A method according to claim 8 in which the metalloendoproteinase is collagenase.

11. A method according to claim 8 in which the metalloendoproteinase is gelatinase.

12. A method for inhibiting the activity of stromelysin comprising administering to a patent suffering from stromelysin mediated disease, a therapeutic amount of the compound of claim 1.

13. A method according to claim 12 wherein the stromelysin inhibitor is administered in an amount of from about 0.01 to 50 mg of the compound per kilogram of body weight per day.

* * * * *